United States Patent [19]

Kudo et al.

[11] Patent Number: 5,195,140
[45] Date of Patent: Mar. 16, 1993

[54] ACOUSTIC SIGNAL PROCESSING APPARATUS

[75] Inventors: Masaki Kudo; Hideaki Shimaya; Tokio Ogi, all of Hamamatsu, Japan

[73] Assignee: Yamaha Corporation, Hamamatsu, Japan

[21] Appl. No.: 635,288

[22] Filed: Dec. 28, 1990

[30] Foreign Application Priority Data

Jan. 5, 1990 [JP] Japan .................................. 2-307

[51] Int. Cl.$^5$ .................. A61F 11/06; H03G 3/00; G06F 7/38
[52] U.S. Cl. ................................. 381/71; 381/63; 84/630; 364/724.03
[58] Field of Search ................ 381/63, 71, 73.1, 94; 84/630, 707; 364/724.03, 724.01

[56] References Cited

U.S. PATENT DOCUMENTS

| | | | |
|---|---|---|---|
| 3,906,199 | 9/1975 | Kieburtz | 364/724.03 |
| 4,034,197 | 7/1977 | Lawrence | 364/724.03 |
| 4,338,581 | 7/1982 | Morgan | 381/63 |
| 4,475,229 | 10/1984 | Frese | 381/63 |
| 4,586,417 | 5/1986 | Kato | 84/630 |
| 4,731,835 | 3/1988 | Futamase et al. | 381/63 |
| 4,868,878 | 9/1989 | Kunugi | 381/1 |

FOREIGN PATENT DOCUMENTS 58-14898 5/1988 Japan .

Primary Examiner—James L. Dwyer
Assistant Examiner—Jack Chiang
Attorney, Agent, or Firm—Graham & James

[57] ABSTRACT

An acoustic signal processing apparatus comprising infinite impulse response type digital filters and phase control device. The filters receive an acoustic signal. Outputs from the filters are synthesized to generate an output signal. The phase control device controls the phase of the output signals so as to cause limit cycle noise components generated by the filters to cancel each other on synthesizing.

10 Claims, 9 Drawing Sheets

IIR FORMULA : y (n) = x (n) + b · y (n − 1)

ACOUSTIC SIGNAL PROCESSING APPARATUS

BACKGROUND OF THE INVENTION

1. Field of the Invention

The present invention relates to an acoustic signal processing apparatus and, more particularly, to an acoustic signal processing apparatus comprising a plurality of infinite impulse response type digital filters, which apparatus can minimize an influence of limit cycle noise generated from each digital filter.

2. Description of the Prior Art

As effector apparatuses for sound sources used in electronic musical instruments, or for the electronic musical instruments, various digital effectors, such as a digital reverberation apparatus, a digital delay apparatus, and the like are known. These apparatuses and various musical tone synthesizing apparatuses adopt many digital filters for controlling frequency characteristics of acoustic signals.

The digital filters can be basically classified to an FIR (finite impulse response) type filter having no signal feedback path, and an IIR (infinite impulse response) type filter having a feedback path. In view of obtained frequency characteristics, an IIR filter can obtain a steep characteristic curve by a relatively simple arrangement (the smaller number of arithmetic elements or the smaller number of multiplications/additions).

As an example of a system which employs many IIR filters, a digital reverberation apparatus (reverberation tone adding apparatus) is known. A typical arrangement of the reverberation tone adding apparatus is disclosed in, e.g., Japanese Patent Laid-Open No. Sho 58-14898.

The IIR filter has a feedback path, and an actual filter processes signals and coefficients having finite word lengths. Therefore, even if an input signal is decreased to zero, an output signal cannot be decreased to zero, and a continuous parasitic oscillation having a predetermined value (DC value) or a predetermined period occurs. This is a problem of a so-called limit cycle.

FIG. 13 shows a typical circuit arrangement of a primary IIR filter. The IIR filter shown in FIG. 13 comprises an adder 21, a memory 22, and a multiplier 23. The memory 22 is a delay memory having two-word storage addresses. This memory 22 is arranged such that when y(n) is written in the memory 22 at present time n, an output signal $y(n-1)$ at immediately preceding time $n-1$ is read out. The immediately preceding output signal $y(n-1)$ is multiplied with an amplitude level control coefficient b by the multiplier 23. The product is inputted to the adder 21. The adder 21 adds the input signal x(n) at time n, and the output $b \cdot y(n-1)$, thereby generating and outputting an output signal y(n). Thus, for an input digital signal x(n) such as amplitude data, an output signal y(n) defined by the following IIR formula, and the immediately preceding output $y(n-1)$ are outputted:

$$y(n) = x(n) + b \cdot y(n-1)$$

A case will be exemplified below wherein a word length of a digital signal to be processed by the primary IIR filter shown in FIG. 13 is represented by B. As is well known, an absolute value of a delayed output $y(n-1)$ is converged to a dead band given by the following equation (1), or oscillates between positive and negative values:

$$|y(n-1)| \leq [0.5 \times 2^{-(B-1)}]/(1-|b|)$$

For example, if $b = +0.75$ and $B = 4$, the absolute value of $y(n-1)$ is converged to a predetermined value $\frac{1}{4}$; when $b = -0.75$ and $B = 4$, it oscillates at an amplitude of $\pm \frac{1}{4}$ and a frequency of $f_s/2$.

In this manner, the IIR filter may keep outputting a predetermined value (DC value), or may oscillate at a frequency of $f_s/2$ ($f_s$: sampling frequency) due to the problem of a finite word length. The filter keeps outputting a limit cycle signal until an input exceeding a dead band value given by equation (1) is supplied.

FIG. 14 is a graph showing input and output signals obtained when a limit cycle of continuously outputting a DC value occurs. At time $T_1$, an input signal SI1 is supplied, and an output signal SO1 is outputted in response thereto. Reference symbol LC10 designates a period in which the limit cycle occurs. During this interval, a predetermined DC value is kept outputted although an input is zero.

FIG. 15 is a graph showing input and output signals obtained when a periodic limit cycle occurs. At given time $T_2$, an input signal SI2 is inputted, and an output signal SO2 is outputted in response to it. LC20 designates a period in which a limit cycle occurs. During this period, signals having a predetermined absolute value, and positive and negative signs are alternately and continuously outputted every sampling time.

In the limit cycle described above, even if an input signal is ended, a very low signal caused by the limit cycle is outputted. Therefore, this signal is equivalent to noise in an acoustic signal processing system. Even if a DC limit cycle occurs, it causes a problem of click noise or a DC level shift in the next circuit. As described above, the IIR filter may be undesirably converted to a kind of noise source due to the limit cycle.

For this reason, in a reverberation tone adding apparatus disclosed in Japanese Patent Laid-Open No. Sho 58-14898 described above, since a large number of IIR filters are connected in parallel with each other in a reverberation tone forming unit, if each filter causes a limit cycle, this results in a decrease in S/N ratio or a narrow dynamic range. On the other hand, in order to eliminate the influence of the limit cycle, a sufficiently large word length can be used. However, in this case, the scale of the arrangement is undesirably increased.

SUMMARY OF THE INVENTION

The present invention has been made in consideration of the conventional problems, and has as its object to provide an acoustic signal processing apparatus which can minimize the influence of the limit cycle occurring in an IIR filter, and allows signal processing having a high S/N ratio without increasing a scale of the arrangement.

In order to achieve the above object, according to the present invention, there is provided an acoustic signal processing apparatus which comprises a plurality of infinite impulse response type digital filters for receiving an acoustic signal, and synthesizes (e.g., adds) outputs from the plurality of infinite impulse response type digital filters to generate an output signal, comprising means for controlling phases of output signals from the infinite impulse response type digital filters so as to cause limit cycle noise components generated by the infinite impulse response type digital filters to cancel each other.

Control of the phases of the output signals from the infinite impulse response type digital filters is realized, for example, by appropriately selecting and setting absolute values and/or signs (±) of coefficients to be multiplied with these output signals.

Furthermore, output signals from the plurality of infinite impulse response type digital filters may be delayed by a predetermined period of time, thereby canceling limit cycle noise components, and generating a synthesized output signal.

With the above arrangement, phases of output signals from the plurality of infinite impulse response type digital filters are controlled, and limit cycle noise components generated in the infinite impulse response type digital filters can be canceled after these outputs are synthesized.

For example, in an acoustic signal processing apparatus for adding and outputting output signals from a plurality of infinite impulse response type digital filters, if limit cycle noise of each infinite impulse response type digital filter is noise of a DC value, as shown in FIG. 14, absolute values and/or signs of coefficients to be multiplied with the output signals from the plurality of infinite impulse response type digital filters are appropriately selected, and after these output signals are added, the limit cycle noise (DC value) can be canceled.

In an acoustic signal processing apparatus for adding and outputting output signals from a plurality of infinite impulse response type digital filters, if oscillating limit cycle noise, as shown in FIG. 15, occurs in each infinite impulse response type digital filter, these output signals are appropriately delayed and then added to each other, so that the limit cycle noise can be canceled.

DETAILED DESCRIPTION OF THE PREFERRED EMBODIMENTS

Figure 1:
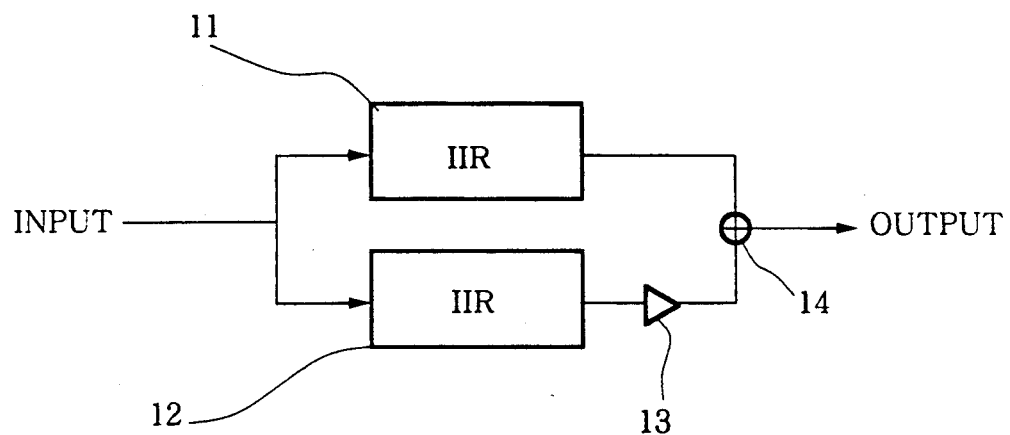
FIGS. 1(a) and 1(b) are block diagrams for explaining the concept of the present invention.
Figure 1:
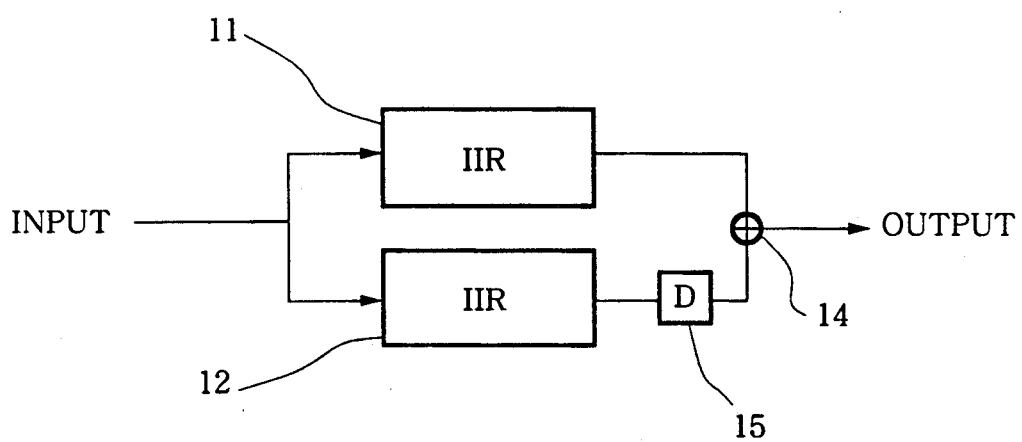

An embodiment of the present invention will be described hereinafter with reference to the accompanying drawings.

The principle of the present invention will be described below with reference to FIGS. 1(a) and 1(b) In FIG. 1(a), infinite impulse response type digital filters (IIR filters) 11 and 12 are connected in parallel with each other. The outputs from these filters are added to each other by an adder 14, thus generating a final output signal. Reference numeral 13 denotes a multiplier for multiplying a predetermined coefficient with the output from the IIR filter 12. This arrangement is used when limit cycle noise generated in the IIR filters 11 and 12 is an output of a predetermined value, as shown in FIG. 14, or when periodic limit cycle noise is generated in an in-phase state, as shown in FIG. 15.

Figure 14:
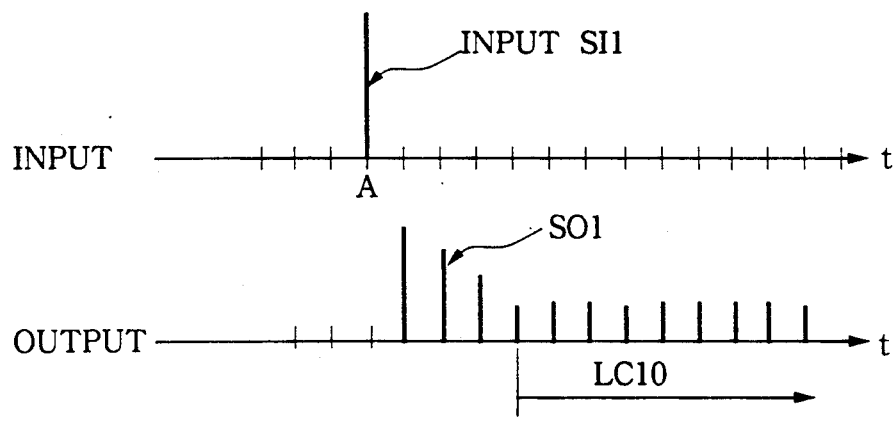
FIGS. 14 and 15 are graphs showing states of generation of limit cycle noise.

A simple example will be described below wherein limit cycle noise components of the IIR filters 11 and 12 are DC values having the same absolute value |a|, as shown in FIG. 14. In this case, if the coefficient to be multiplied by the multiplier 13 is −1, a limit cycle noise component +|a| is outputted from the IIR filter 11 during a limit cycle period, and the multiplier 13 outputs a signal −|a| obtained by multiplying the coefficient "−1" with the limit cycle noise from the IIR filter 12. Therefore, these limit cycle noise components cancel each other in the adder 14, and an output signal becomes zero.

Figure 15:
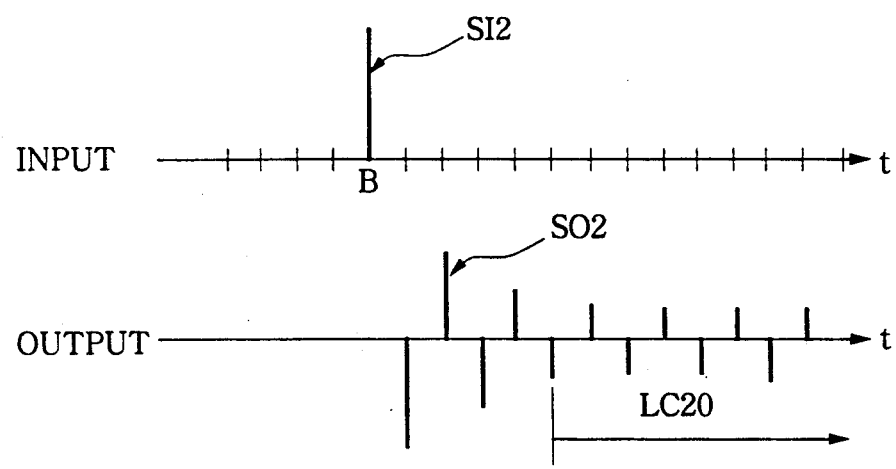

Similarly, when the IIR filter 11 generates periodic limit cycle noise shown in FIG. 15, and the IIR filter 12 generates limit cycle noise having the same phase and the same amplitude as those of the noise generated by the filter 11, if the coefficient of the multiplier 13 is set to be −1, these limit cycle noise components cancel each other in the adder 14, and an output signal becomes zero.

The coefficient of the multiplier 13, i.e., an absolute value to be multiplied and/or a sign can be appropriately selected to cause limit cycle noise components to cancel each other. When constants of the IIR filter are determined, a type of limit cycle noise generated by the filter can be determined beforehand by calculations. Therefore, when a combination of IIR filters and the way of synthesizing outputs from the IIR filters are determined, the coefficient of the multiplier can be determined.

In FIG. 1(b), an output from the IIR filter 11, and an output obtained by delaying an output from the IIR filter 12 by a predetermined period of time by a delay circuit 15 are added to each other by the adder 14, thus generating a final output. For example, if limit cycle noise components generated by the IIR filters 11 and 12 are periodic noise components having the same phase and the same amplitude, as shown in FIG. 15, the output from one IIR filter 12 is delayed by one sampling period by the delay circuit 15, thereby canceling these limit cycle noise components by the adder 14.

Assuming that IIR filters are applied to, e.g., a reverberation circuit, even when the multiplier 13 or the delay circuit 15 is arranged, as described above, these components do not significantly influence reverberation characteristics of a reverberation tone signal output before a period in which limit cycle noise is generated.

Figure 2:
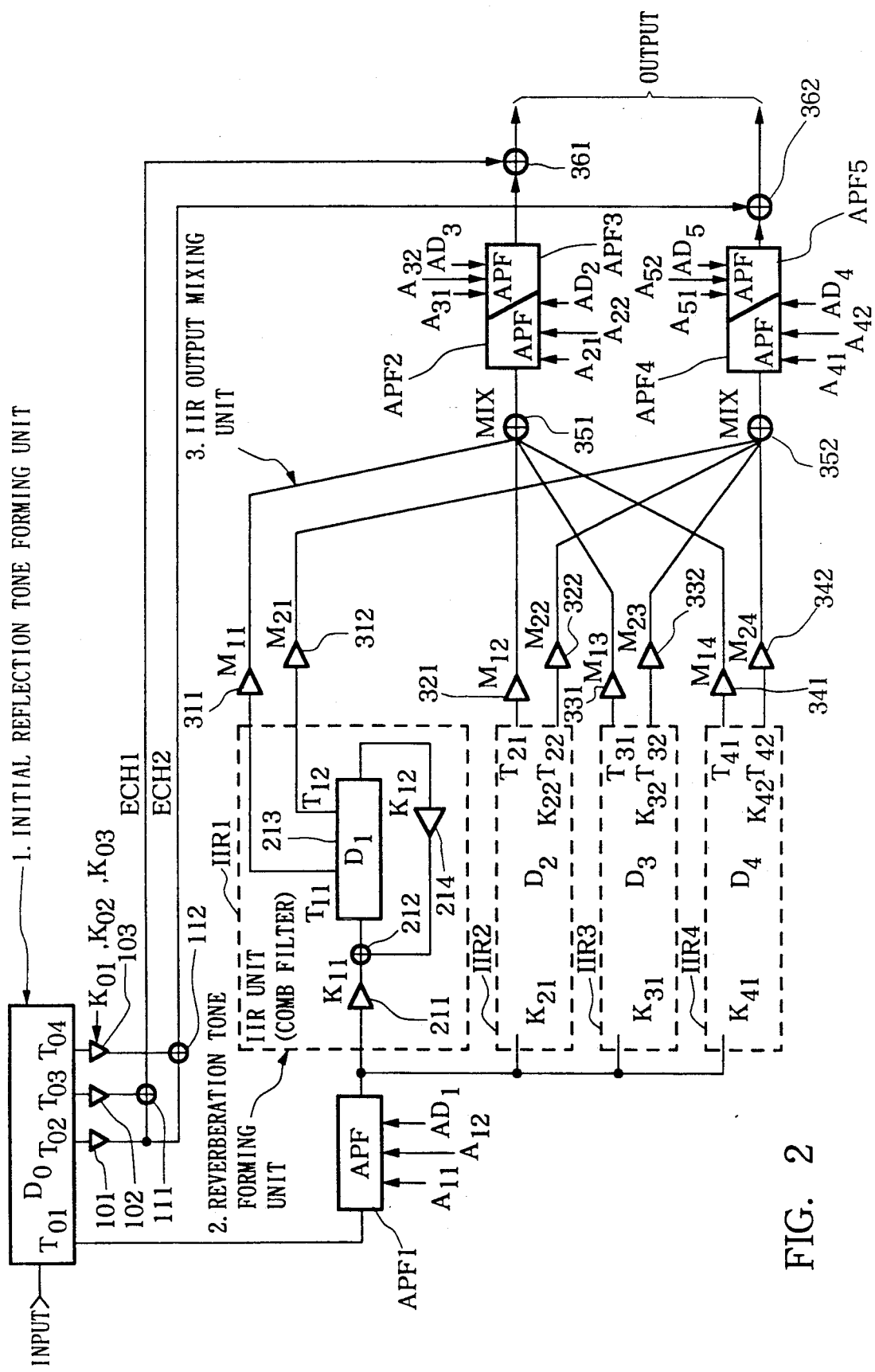
FIG. 2 is a block diagram showing an arrangement of an acoustic signal processing apparatus according to an embodiment, of the present invention.

FIG. 2 is a block diagram of an acoustic signal processing apparatus according to an embodiment of the present invention. In this circuit, the acoustic signal processing apparatus of the present invention is applied to a reverberation tone adding apparatus.

In FIG. 2, amplitude data (digital data) obtained by sampling an acoustic signal for a predetermined cycle is inputted to an initial reflection tone forming unit 1. Since the initial reflection tone forming unit 1 comprises an FIR filter, no limit cycle noise is generated. In the circuit shown in FIG. 2, an acoustic signal and a coefficient word length as digital data are assumed to have a predetermined finite number of bits.

The initial reflection tone forming unit 1 comprises a memory D0 having a predetermined number of (e.g., 2,048) storage addresses, multipliers 101, 102, and 103 connected to taps T02, T03, and T04 arranged at predetermined address positions of the memory D0, an adder 111 for adding outputs from the multipliers 101 and 102 and outputting initial reflection tone data ECH1, and an adder 112 for adding outputs from the multipliers 101 and 103 and outputting initial reflection tone data ECH2. The positions of the taps T02, T03, and T04 of the memory D0, and coefficients K01, K02, and K03 of the multipliers 101, 102, and 103 are determined in accordance with an initial reflection tone to be obtained.

An output from the tap T01 of the initial reflection tone forming unit 1 is inputted to a reverberation tone forming unit 2 via an all-pass filter APF1. The reverberation tone forming unit 2 forms a reverberation tone following the initial reflection tone.

Figure 3:
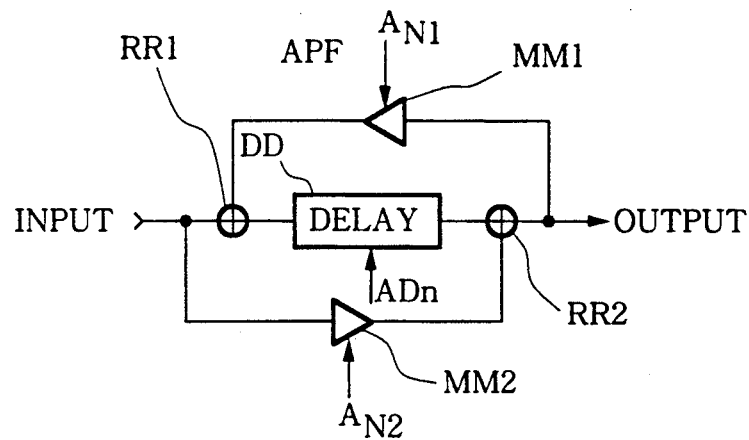
FIG. 3 is a block diagram of an all-pass filter.

The all-pass filter APF1 is a delay circuit having flat frequency characteristics, and is arranged, as shown in FIG. 3.

Referring to FIG. 3, before input data to the all-pass filter APF1 is supplied to an adder RR1, an address ADn for reading out data written in a delay memory DD, having storage addresses of the predetermined number of words, a predetermined period of time before is designated. Thus, data which was written the predetermined period of time before (data at the address ADn) is read out from the delay memory DD, and is inputted to an adder RR2. The input data to the all-pass filter APF1 is multiplied with a predetermined amplitude level control coefficient AN2 by a multiplier MM2, and the product is inputted to the adder RR2. The adder RR2 adds the data which is delayed by the predetermined period of time and is read out from the address ADn of the memory DD, and the output data from the multiplier MM2, and the sum is outputted as output data of the all-pass filter APF1 at present time. This output data is multiplied with an amplitude level control coefficient AN1 by a multiplier MM1, and the product is fed back to the adder RR1. The adder RR1 adds this feedback data, and the data supplied at the present time, and stores the sum at an address position of the delay memory DD at the present time. In this manner, an output signal of the all-pass filter APF1 is generated.

Referring back to FIG. 2, the output from the all-pass filter APF1 is inputted to infinite impulse response filters IIR1 to IIR4 constituting the reverberation tone forming unit 2. These filters IIR1 to IIR4 are delay circuits using comb filters and having different delay times. In this case, four circuits are arranged in parallel with each other.

The filter IIR1 comprises a memory D1, having a predetermined word length, for obtaining a predetermined delay time, a multiplier 211, an adder 212, and a multiplier 214. An input to the filter IIR1 is multiplied with an amplitude level control coefficient K11 by the multiplier 211. The product is inputted to the adder 212. At this time, amplitude data written in the memory D1 having storage addresses of the predetermined word length a predetermined period of time before is read out, and is multiplied with an amplitude level control coefficient K12 by the multiplier 214. The product is inputted to the adder 212. The adder 212 adds the input from the multiplier 211, and the delayed input from the multiplier 214. The sum is written at a given address of the memory D1 where present time data is to be written. Output taps T11 and T12 are arranged at appropriate address positions of the memory D1, and output signals are outputted from these taps T11 and T12.

The filters IIR2 to IIR4 arranged in parallel with the filter IIR1 have the same arrangement as that of the filter IIR1. Note that coefficients, tap positions, and the like of these filters IIR1 to IIR4 are appropriately selected to obtain desired delay signals.

Outputs from the filters IIR1 to IIR4, i.e., acoustic signals with reverberation tones are inputted to an IIR output mixing unit 3. In the IIR output mixing unit 3, the output signals from the filters IIR1 to IIR4 are multiplied with predetermined coefficients (predetermined absolute values and signs, as will be described later) by multipliers 311, 312, 321, 322, 331, 332, 341, and 342. These products are added by adders 351 and 352.

Coefficients M11, M12, M13, and M14 of the multipliers 311, 321, 331, and 341 are appropriately selected so as to cancel limit cycle noise components generated in the filters IIR1 to IIR4 upon an addition by the adder 351 as much as possible. Thus, the influence of limit cycle noise in the output from the adder 351 can be minimized. Similarly, coefficients M21, M22, M23, and M24 of the multipliers 312, 322, 332, and 342 are appropriately selected so as to cancel limit cycle noise components generated in the filters IIR1 to IIR4 upon an addition by the adder 352 as much as possible. Thus, the influence of limit cycle noise in the output from the adder 352 can be minimized.

The output signal from the adder 351 is inputted to an adder 361 via all-pass filters APF2 and APF3. The adder 361 adds the output ECH1 from the initial reflection tone forming unit 1, and the output from the all-pass filter APF3, thus outputting a final acoustic signal (reverberation tone added signal). Similarly, the output signal from the adder 352 is inputted to an adder 362 via all-pass filters APF4 and APF5. The adder 362 adds the output ECH2 from the initial reflection tone forming unit 1, and the output from the all-pass filter APF5, thus outputting a final acoustic signal (reverberation tone added signal).

This embodiment adopts two-system outputs since respective channels are driven with a predetermined delay time to attain a pseudo stereophonic effect.

Figure 4:
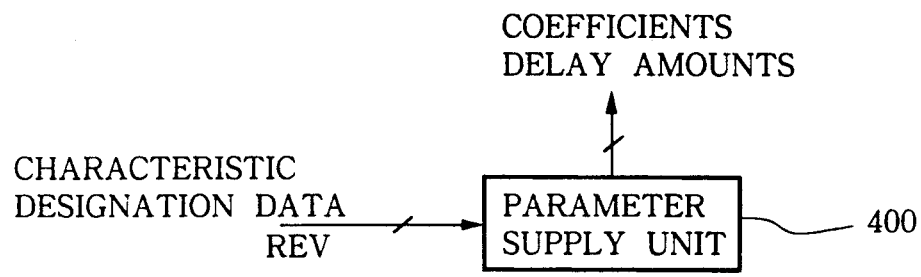
FIG. 4 is a block diagram of a parameter supply unit.

In the circuit shown in FIG. 2, coefficients and delay times are supplied from a parameter supply unit. FIG. 4 shows the parameter supply unit.

The parameter supply unit 400 receives characteristic designation data REV for designating characteristics of a reverberation tone, and outputs data for specifying coefficients and delay times of the circuit shown in FIG. 2 on the basis of the input data.

Figure 5:
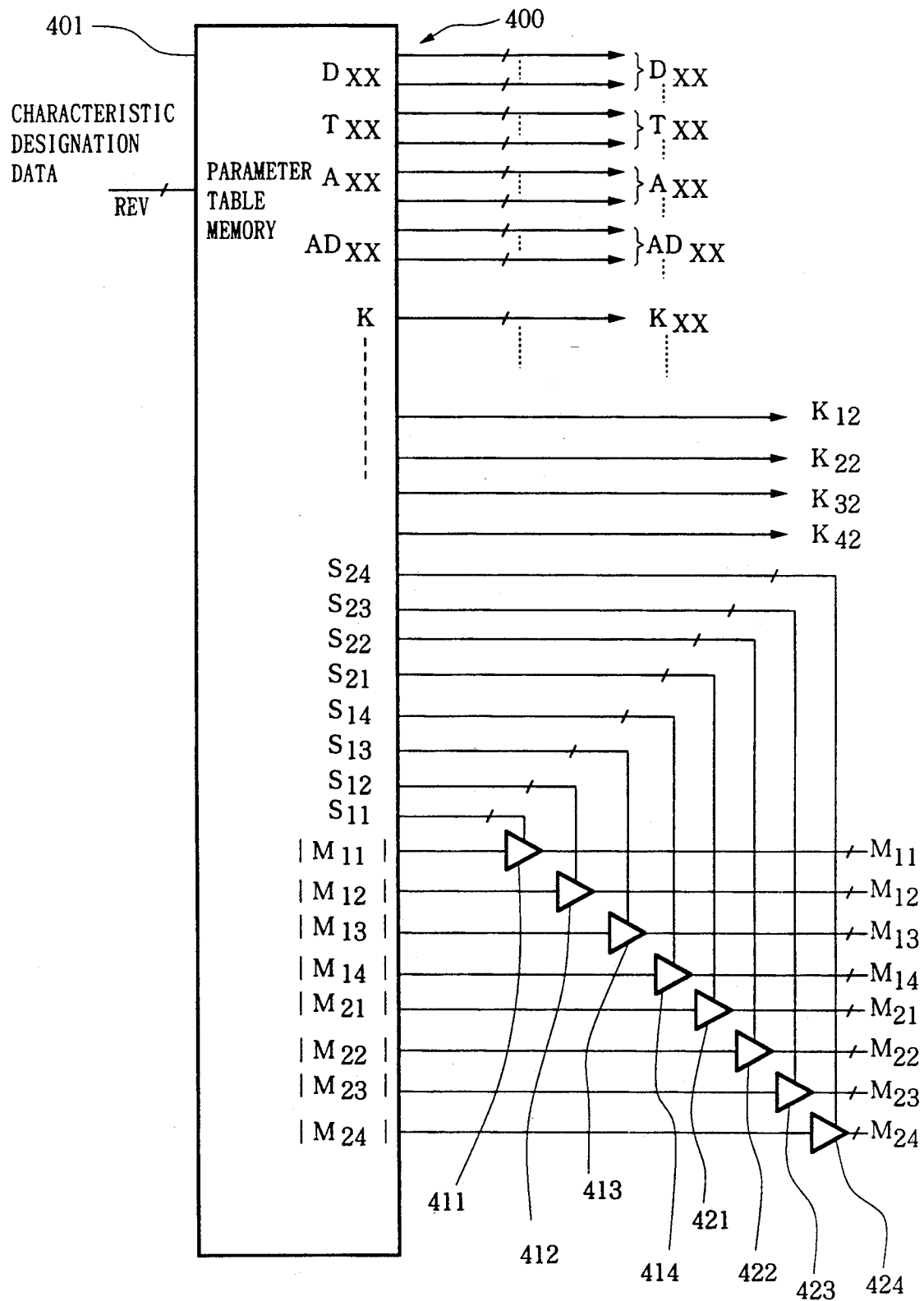
FIG. 5 is a detailed block diagram of the parameter supply unit.

FIG. 5 is a detailed circuit diagram of the parameter supply unit 400. The parameter supply unit 400 comprises a parameter table memory 401, and multipliers 411 to 424. The parameter table memory 401 receives the characteristic designation data REV, and outputs coefficients and delay amounts according to the input data.

Data Dxx outputted from the parameter table memory 401 are parameters for specifying delay times of the delay memories D0 to D4. Reference symbol Txx denotes parameters for designating tap positions of the delay memories D0 to D4; Axx, amplitude level control parameters for the all-pass filters APF1 to APF5; ADxx, parameters indicating read address positions of the delay memories of the all-pass filters APF1 to APF5; and Kxx, parameters representing multiplication coefficients of the multipliers 101 to 103 and the multipliers in the filters IIR1 to IIR4.

The multipliers 411 to 414 and 421 to 424 are multipliers for determining the signs (polarities) of the multiplication coefficients M11 to M14 and M21 to M24 of the multipliers 311, 312, 321, 322, 331, 332, 341, and 342 in the circuit shown in FIG. 2. These multipliers 411 to 414 and 421 to 424 provide signs to absolute values |M11| to |M14|, and |M21| to |M24| on the basis of sign control data S11 to S14 and S21 to S24 outputted from the parameter table memory 401. More specifically, the multiplication coefficients of these multipliers 411 to 414 and 421 to 424 are corresponding ones of $+1$ and $-1$ on the basis of the sign control data S11 to S14 and S21 to S24.

When the coefficients K12, K22, K32, and K42 of the multipliers in the filters IIR1 to IIR4 are determined, limit cycle characteristics of the filters IIR1 to IIR4 are determined. Therefore, the sign control data S11 to S14 and S21 to S24 can be determined on the basis of the coefficients K12, K22, K32, and K42. More specifically, since a signal word length and a coefficient word length of each IIR filter have the predetermined finite number of bits, whether DC or periodic ($f_s/2$) limit cycle occurs can be determined on the basis of the relationship among the number of bits and the coefficients K12, K22, K32, and K42 (equation (1)). For example, in the embodiment shown in FIG. 2, when the multiplication coefficients K12, K22, K32, and K42 are determined according to the characteristic designation data REV, the limit cycle characteristics of the corresponding filters IIR1 to IIR4 are determined.

When all the four systems of IIR filters cause a DC limit cycle, the multiplication coefficients Mxx are selected to make a DC offset caused by the limit cycle zero in outputs of the mixing stages (adders 351 and 352), thereby canceling the limit cycle. Alternatively, if absolute values of coefficients are not to be changed, only the polarities (signs) of the coefficients may be changed to minimize the influence of the limit cycle.

If there is an IIR filter which causes a periodic limit cycle at $f_s/2$, similarly, the coefficients can be set and selected, or combinations of signs of coefficients can be appropriately selected so as to make zero or minimize the influence of the limit cycle.

Figure 6:
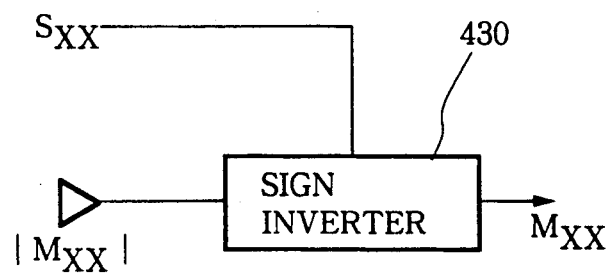
FIG. 6 is a block diagram showing a state wherein a sign of a coefficient Mxx is inverted using a sign inverter.

In FIG. 5, optimal sign control data (polarity designation data) Sxx are read out and supplied together with reverberation parameters corresponding to the characteristic designation data REV. When the multipliers 411 to 414 and 421 to 424 are used, data Sxx are $+1$ or $-1$. When the multiplication coefficients of the multipliers are $-1$, a sign inverter may be used in place of the multipliers. FIG. 6 shows a modification employing a sign inverter 430. When the sign inverter 430 is to be controlled, sign control data Sxx becomes logic "0" or "1".

Figure 7:
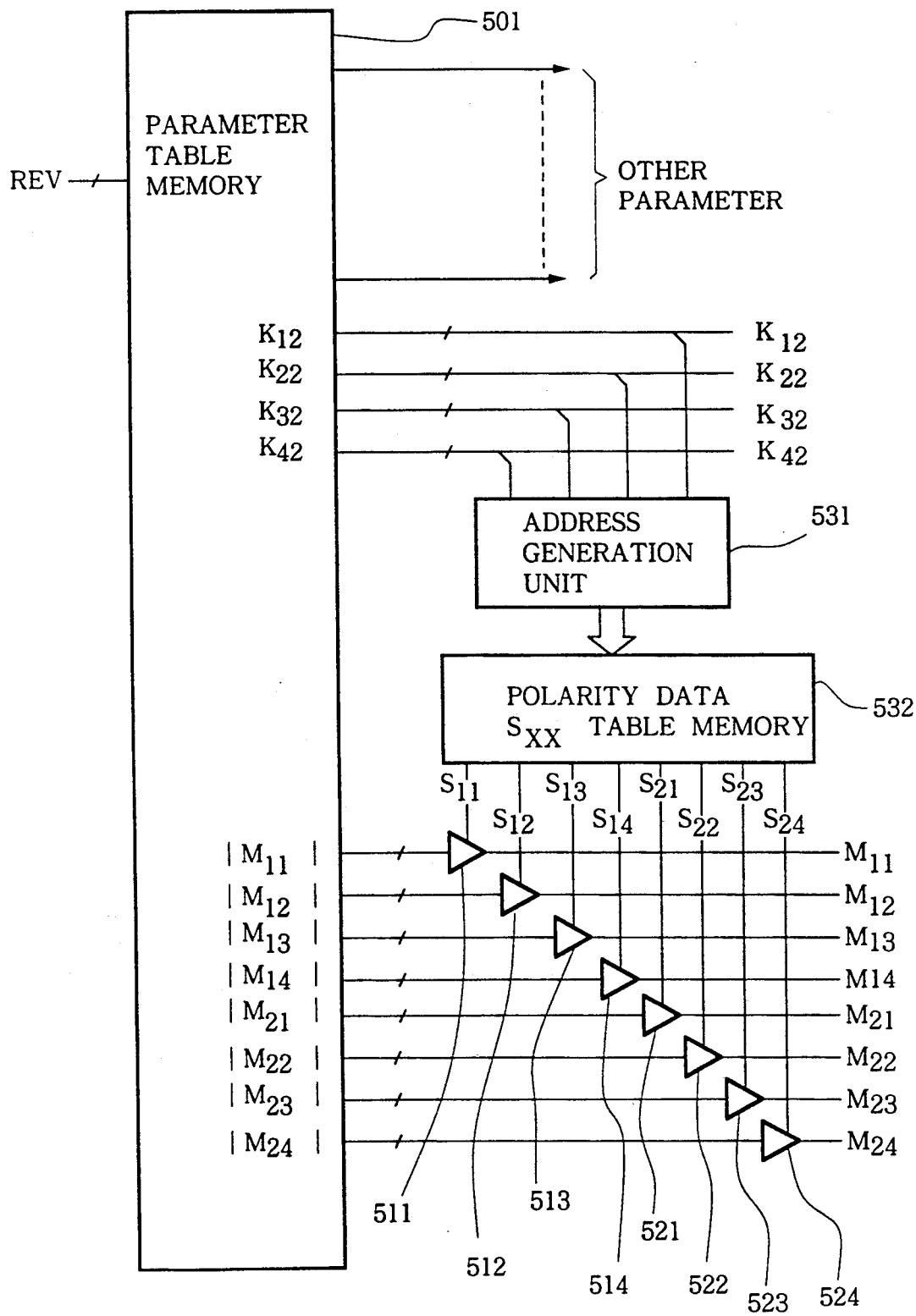
FIG. 7 is a block diagram of a parameter supply unit of an acoustic signal processing apparatus according to the second embodiment of the present invention.

FIG. 7 shows a case wherein polarity designation data Sxx of optimal multiplication coefficients (mixing coefficients) are read out from a multiplication coefficient table which uses a combination of coefficients Kn2 ($n=1$ to 4) as an address, thus optimizing control.

An address generation unit 531 generates an address for accessing a polarity data Sxx table memory 532 on the basis of the coefficient values Kn2 outputted from a parameter table memory 501 in accordance with characteristic designation data REV. The polarity data Sxx table memory 532 stores polarity data Sxx at predetermined address positions specified by combinations of the coefficient values Kn2. Therefore, polarity data Sxx according to the coefficient values Kn2 are inputted to multipliers 511 to 514 and 521 to 524, so that signs are provided to absolute values |M11| to |M14| and |M21| to |M24| of the coefficients, thereby outputting the coefficients.

Figures 8, 9:
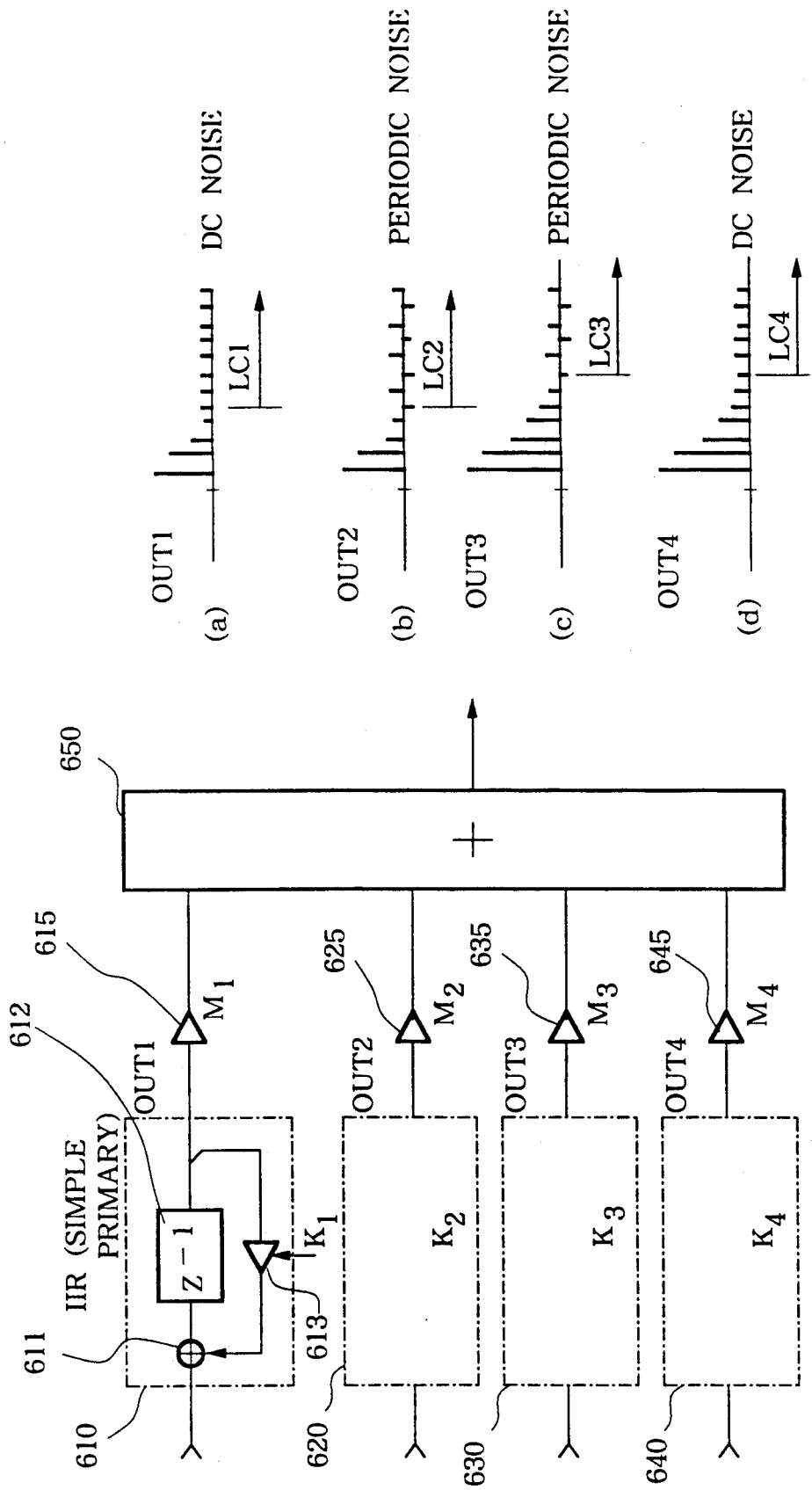
FIG. 8 is a block diagram for explaining an operation for canceling limit cycle noise.
FIG. 9 is a graph showing limit cycle noise generated in each filter in the circuit shown in FIG. 8.

An operation for canceling a limit cycle will be described below with reference to FIGS. 8 to 9(d). FIG. 8 shows a case wherein predetermined coefficients M1 to M4 are multiplied with outputs OUT1 to OUT4 of four IIR filters 610, 620, 630, and 640 by multipliers 615, 625, 635, and 645, and the products are mixed by an adder 650 to obtain a final output. The IIR filter 610 is a simple primary filter, and comprises an adder 611, a delay memory 612, and a multiplier 613. The filters 620, 630, and 640 have the same arrangement as the filter 610.

Assume that the IIR filter 610 generates DC limit cycle noise, as shown in FIG. 9(a). In FIG. 9(a), LC1 designates a generation period of the limit cycle. Similarly, assume that IIR filters 620, 630, and 640 generate limit cycle noise components, as shown in FIGS. 9(b), 9(c), and 9(d). More specifically, assume that the IIR filters 610 and 640 generate DC limit cycle noise, and the IIR filters 620 and 630 generate periodic limit cycle noise.

At this time, if the amplitudes of the limit cycle noise components are equal to each other, the coefficients can be set as follows:

M1 = +0.25

M2 = +0.25

M3 = −0.25

M4 = −0.25

In this case, the limit cycle noise components are canceled by the adder 650, and its output becomes zero. In this manner, the influence of limit cycle noise can be eliminated.

In the above embodiment, the influence of the limit cycle noise is minimized under the control of only polarities (signs) of mixing coefficients. For example, original setup values of associated parameters such as coefficient values, delay tap positions (for canceling periodic limit cycle noise in terms of phases), and the like are properly corrected within a predetermined allowable range (within a range which does not largely fall outside desired acoustic characteristics), thereby further reducing the influence of limit cycle noise.

Figure 10:
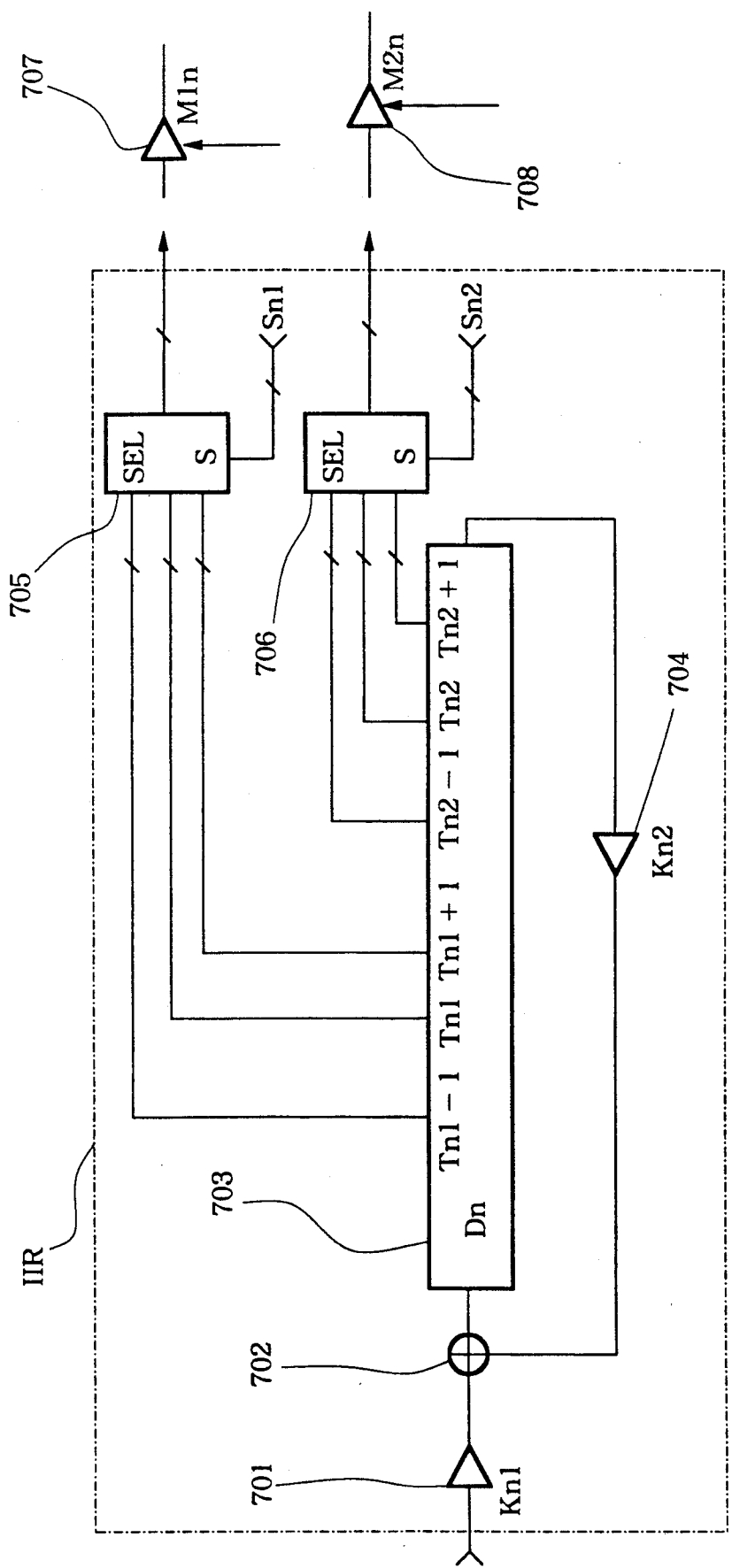
FIG. 10 is a block diagram showing an embodiment wherein a delay time of an IIR filter can be selected.

FIG. 10 shows a case wherein tap positions of a delay memory in an IIR filter are appropriately selected to eliminate the influence of limit cycle noise.

The IIR filter shown in FIG. 10 comprises a multiplier 701, an adder 702, a delay memory 703, and a multiplier 704. These components are the same as those in the above embodiment. The output from the IIR filter is obtained from appropriate tap positions of the delay memory 703. Outputs from delay tap positions $Tn_1-1$, $Tn_1$, and $Tn_1+1$ are inputted to a selector 705. The selector 705 selects one of the three tap positions on the basis of a parameter $Sn_1$ outputted from a parameter supply unit, and outputs it as an output signal. Similarly, outputs from three tap positions $Tn_2-1$, $Tn_2$, and $Tn_2+1$ are inputted to a selector 706. The selector 706 selects one of these tap positions in accordance with a parameter $Sn_2$ from the parameter supply unit, and outputs it as an output signal. Multipliers 707 and 708 are those corresponding to the multipliers 311, 312, and the like shown in FIG. 2.

According to the IIR filter shown in FIG. 10, delay times are determined in accordance with the parameters $Sn_1$ and $Sn_2$ supplied from the parameter supply unit. Therefore, if the parameters $Sn_1$ and $Sn_2$ according to the characteristics of the IIR filter are selected, the influence of limit cycle noise can be consequently minimized.

Figure 11:
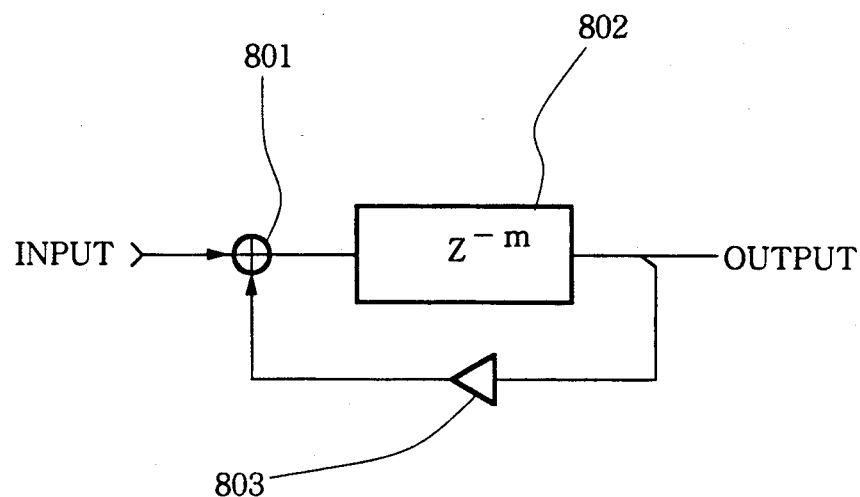
FIG. 11 is a block diagram of a filter for performing an m-stage delay operation.

In an IIR filter having a feedback circuit using a plurality of delay stages, as shown in FIG. 11, an effective sampling frequency is decreased by the number of delay stages. Therefore, an output cycle of the limit cycle noise corresponds to the decreased sampling frequency.

Figure 12:
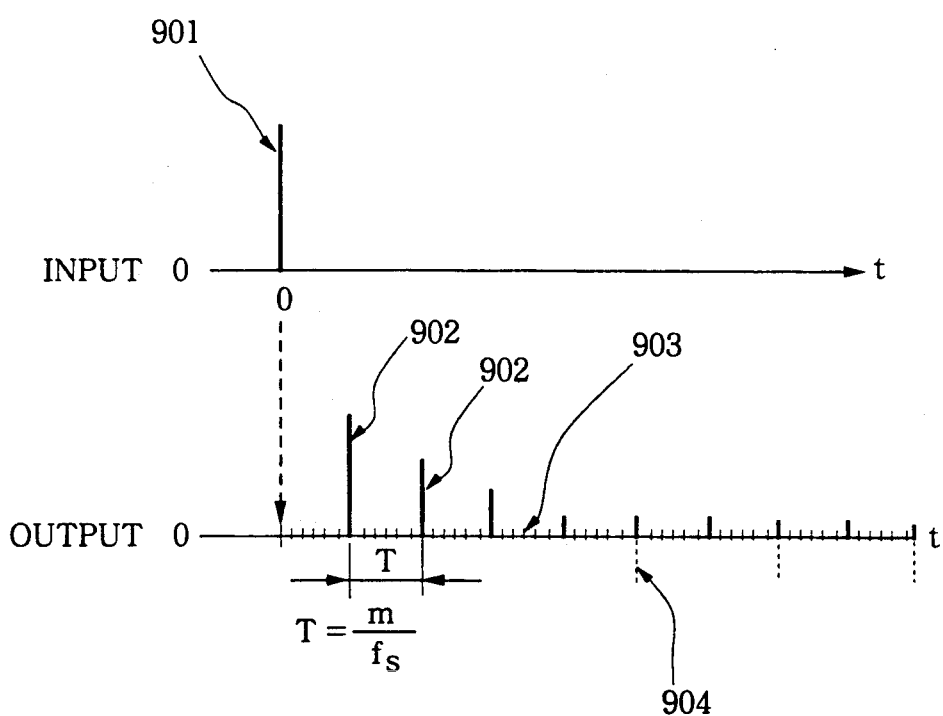
FIG. 12 is a graph showing a state wherein signals are sampled using the filter shown in FIG. 11.
Figure 13:
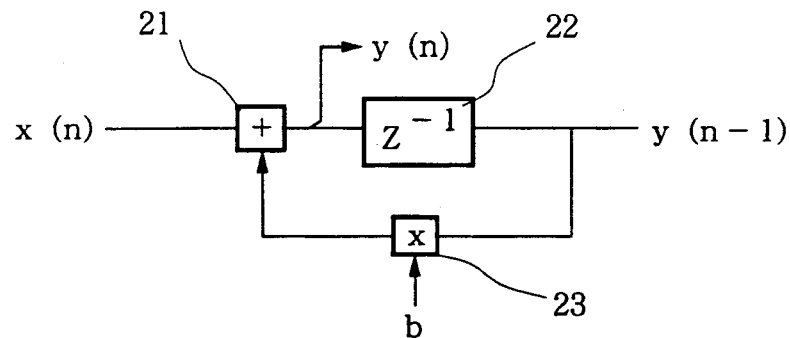
FIG. 13 is a circuit diagram showing a typical arrangement of a primary IIR filter.

FIG. 11 shows a primary IIR filter having a plurality of delay stages. The IIR filter comprises an adder 801, a memory 802 for realizing m delay stages, and a multiplier 803. A sampling frequency is $1/f_s$. In this case, as shown in FIG. 12, output samples 902 are outputted for a cycle of $m/f_s$ in response to an input signal 901. Outputs at a sample time between these output samples 902 are zero. Therefore, in this case, noise is reduced, or limit cycle noise is scattered between positive and negative levels, or generation of limit cycle noise which can be regarded as a kind of pulses is scattered along the time base (phases are slightly shifted by delays), so that the noise can be converted to one which does not easily strike ears (e.g., white noise).

In the above embodiment, optimal parameters are outputted from a table. For example, a means for quantitatively analyzing a limit cycle may be arranged, so that optimization may be attained after various arithmetic analysis operations.

In the above embodiment, a reverberation tone adding apparatus has been exemplified. However, the present invention is not limited to the reverberation adding apparatus, by may be applied to a tone color adjusting apparatus for an electronic musical instrument, and various other signal processing apparatuses.

The above embodiment has been described as hardware. However, signal processing or coefficient supply algorithms may be realized by software using various computers, DSPs (digital signal processors), and the like.

As described above, according to the present invention, when output signals from a plurality of signal paths including IIR filters are mixed, mixing coefficients are selected and set according to IIR filter coefficients to minimize the influence of limit cycle noise. Therefore, a musical tone signal processing apparatus which can attain signal processing with a high S/N ratio without increasing its scale can be provided.

What is claimed is:

1. An acoustic signal processing apparatus comprising:
   a plurality of infinite impulse response type digital filters for filtering an acoustic signal, each of said plurality of infinite impulse response type digital filters having an input for receiving said acoustic signal and an output for generating a filtered output signal in response to said acoustic signal;
   phase control means for controlling relative phases of said filtered output signals to provide phase controlled output signals from said infinite impulse response type digital filters; and
   mixing means for respectively mixing said phase controlled output signals to substantially cancel a limit cycle noise component generated by said plurality of infinite impulse response type digital filters.

2. An apparatus according to claim 1, wherein said phase control means appropriately selects at least one of absolute values and signs of coefficients to be multiplied with said filtered output signals from said plurality of infinite impulse response type digital filters.

3. An apparatus according to claim 1, wherein said phase control means delays said filtered output signal from at least one of said plurality of infinite impulse response type digital filters.

4. An apparatus according to claim 2, wherein said limit cycle noise component is of a DC value.

5. An apparatus according to claim 3, wherein said limit cycle noise component is an oscillating limit cycle noise.

6. An apparatus according to claim 1, wherein the acoustic signal processing apparatus is applied to a reverberation tone adding apparatus.

7. An apparatus according to claim 2, wherein said phase control means delays said filtered output signal from at least one of said plurality of infinite impulse response type digital filters.

8. An apparatus according to claim 1, wherein said phase control means inverts a sign of said filtered output signal from at least one of said plurality of infinite impulse response type digital filters.

9. An apparatus according to claim 1, wherein said phase control means multiplies coefficients with said filtered output signals from said plurality of infinite impulse response type digital filters.

10. An apparatus according to claim 1, wherein said phase control means appropriately selects signs of coefficients to be multiplied with said filtered output signals from said plurality of infinite impulse response-type digital filters.

* * * * *